(12) United States Patent
Lewis

(10) Patent No.: US 7,413,597 B2
(45) Date of Patent: Aug. 19, 2008

(54) IMAGING POWDER FOR CAD/CAM DEVICE

(76) Inventor: Elaine Lewis, 5460 Lakeside Dr., Fairfield, OH (US) 45014

( * ) Notice: Subject to any disclaimer, the term of this patent is extended or adjusted under 35 U.S.C. 154(b) by 134 days.

(21) Appl. No.: 11/348,844

(22) Filed: Feb. 7, 2006

(65) Prior Publication Data

US 2007/0095251 A1    May 3, 2007

Related U.S. Application Data

(60) Provisional application No. 60/733,326, filed on Nov. 30, 2005.

(51) Int. Cl.
| | |
|---|---|
| *C09K 3/00* | (2006.01) |
| *A61C 15/04* | (2006.01) |
| *A61C 5/00* | (2006.01) |
| *B65B 33/00* | (2006.01) |
| *A61B 5/117* | (2006.01) |
| *C08L 1/00* | (2006.01) |
| *C08L 3/00* | (2006.01) |
| *C08L 5/00* | (2006.01) |
| *C09J 103/00* | (2006.01) |

(52) U.S. Cl. .................. 106/35; 427/2.29; 427/154; 427/155; 433/217.1; 433/229; 106/162.9; 106/215.2; 106/217.3; 106/217.7

(58) Field of Classification Search .............. 424/70.13; 433/203.1, 217.1, 229; 427/2.17, 154, 155; 106/35, 215.2, 217.3, 217.7, 217.9, 162.9
See application file for complete search history.

(56) References Cited

U.S. PATENT DOCUMENTS

| | | | |
|---|---|---|---|
| 3,488,204 A * | 1/1970 | Hardy et al. ............... 106/447 |
| 5,338,198 A | 8/1994 | Wu et al. |
| 5,386,292 A | 1/1995 | Massen et al. |
| 5,944,521 A | 8/1999 | Lawler |
| 6,099,306 A | 8/2000 | Lawler |
| 6,294,013 B1 * | 9/2001 | Ortlano et al. ............. 106/499 |
| 6,416,322 B2 | 7/2002 | Qualliotine et al. |
| 6,854,973 B2 | 2/2005 | Butcher et al. |
| 6,878,456 B2 | 4/2005 | Castro et al. |
| 2005/0019724 A1 | 1/2005 | Lawler |
| 2005/0233280 A1 | 10/2005 | Hamman |
| 2005/0250070 A1 | 11/2005 | Hamman |

* cited by examiner

*Primary Examiner*—Jerry Lorengo
*Assistant Examiner*—Noah S Wiese
(74) *Attorney, Agent, or Firm*—Frost Brown Todd LLC

(57) ABSTRACT

The present invention relates to an imaging powder for dental restoration using a CAD/CAM device, wherein the powder has improved properties as compared to existing contrast media. The present invention also relates to a method of making and using the imaging powder for use with the CAD/CAM dental imaging device.

13 Claims, No Drawings

IMAGING POWDER FOR CAD/CAM DEVICE

This application claims priority under 35 U.S.C. §119 to U.S. Provisional Application No. 60/733,326, filed Nov. 30, 2005.

FIELD OF INVENTION

This invention relates to a composition used as an imaging powder for a CAD/CAM device. More particularly, the present invention is a contrast medium for dental restoration using a CAD/CAM device, wherein the contrast medium has improved properties as compared to existing contrast media. The present invention also relates to a method of making such an imaging powder having a preferred particle size and its use with a CAD/CAM dental imaging device.

BACKGROUND

CAD/CAM (Computer-Aided Design/Computer-Aided Manufacturing) is used to obtain digital images of a target object. In the dental field, CAD/CAM technology is of particular importance. CAD/CAM systems, such as the CEREC (Chairside Economical Restoration of Esthetic Ceramics) System manufactured by Siemens Dental Products Division and the PROCERA A11-Ceram system of Nobel Biocare AD, are used to obtain optical impressions of cavity preparations for restorative work. These impressions can then be used for the manufacture of inlays, onlays, partial crowns, posterior crowns, anterior crowns and veneers.

The CAD/CAM camera takes a three dimensional image of the target area using infrared waves that are sent down to the area and back to the camera. An optical image is recorded with the 3D camera by projecting an invisible grid onto the field of view to record surface dimensions. As the grid is reflected off the surface, the camera interprets distortions in the grid as differences in height (Z values). The camera's field of view must have a uniform reflective surface to accurately record the height values. With respect to dental applications, computational analysis of the data captured by the optical image of a tooth allows for precise measurement of the heights of the structure, adjacent teeth and surrounding tissue. Accurate recording of the preparation is essential to effective application of the device.

SUMMARY OF THE INVENTION

This invention relates to an imaging powder for use in a CAD/CAM device. The powder comprises from about 15% to about 50% w/w of a polysaccharide, from about 7% to about 25% w/w of zirconium oxide, from about 1% to about 10% w/w talc, from about 9% to about 25% w/w lactose, from about 15% to about 35% w/w titanium dioxide, and from about 1% to about 10% w/w zinc oxide. The polysaccharide may be corn starch. In one embodiment, about 90% of the powder has a particle size equal to or less than about 40 microns. In another embodiment, 90% of the powder has a particle size equal to or less than about 20 microns. The imaging powder is applied to a tooth via a stream of compressed air, wherein the applied powder is of appropriate thickness in order to obtain a suitable image using a CAD/CAM device.

Alternatively, the imaging powder for use in a CAD/CAM device may comprise from about 30% to about 35% w/w of a polysaccharide, from about 13% to about 15% w/w of zirconium oxide, from about 20% to about 25% w/w talc, from about 23% to about 28% w/w titanium dioxide, and from about 3% to about 5% w/w zinc oxide, wherein the polysaccharide is corn starch and the powder. In one embodiment, about 90% of the powder has a particle size equal to or less than about 40 microns. In another embodiment, 90% of the powder has a particle size equal to or less than 20 about microns. The powder is applied to a tooth via a stream of compressed air, and the applied powder is of appropriate thickness, as determined by one skilled in the art, in order to obtain a suitable image of the tooth using the CAD/CAM device.

DETAILED DESCRIPTION OF THE INVENTION

Imaging for dental applications requires uniform reflection of the target surfaces and accurate imaging. However, dentin, enamel, and gingival absorb the infrared waves at different rates. As such, typically, to create a uniformly reflective surface, a thin layer of non-toxic, titanium dioxide powder is applied to the area to be imaged and neighboring teeth. This contrast medium currently available in the art consists of a powder comprised of titanium oxide, talc, and zirconium. [Vita® and ProCad Powders®.] This powder can be applied in conjunction with a polysorbate liquid. The liquid is applied liberally to the tooth and surrounding areas to provide a sticky film for adhesion of the titanium powder. The resulting layer of polysorbate liquid and titanium dioxide creates uniformity of reflective properties of the teeth and surrounding areas and ensures an accurate determination of the Z values of the cavity preparation.

The powder available in the art is such that many additional steps must be taken to optimize performance. First, the polysorbate liquid must be applied prior to application of the powder. The powder should be sifted prior to use because of clumping during the application process. It is also recommended that the powder be microwaved prior to use. Finally, post-imaging removal of the powder is made more difficult because of the adhesive properties of the polysorbate liquid.

The titanium powder is typically applied by specialized application devices, for example, the Powder-Meister® Powder Applicator for Teeth, the subject of US Application No. 20050233280 (which is herein incorporated by reference), the Powder-Perfect® device, canned air, an apparatus connected to a high speed air line or any type of air method.

The powdering of the tooth is a step in the imaging process. Note that over and under-powdering can interfere with accurate imaging. Therefore, care must be taken to avoid an uneven coating of the powder that would interfere with the 3D imaging; under-powdering should also be avoided. It will be obvious to one skilled in the art as to the requisite thickness the powder must be on the tooth surface for proper imaging. Areas that appear very dark in the optical impression are generally a result of inadequate powdering. Successful powdering results in an image that is clear and focused, with visible margins and corners, without powder "spikes" or dark areas.

Method of Making Imaging Powder

The present invention comprises the following substances which are combined together at room temperature to form a homogeneous mixture:

| Dry mix | % by Weight |
| --- | --- |
| Polysaccharide (for example, corn starch) | From about 15% to about 50%; also from about 25% to about 40%; and also from about 30% to about 35% |
| Zirconium Oxide | From about 7% to about 25%; also from about 10% to about 20%; and also from about 13% to about 15% |

-continued

| Dry mix | % by Weight |
| --- | --- |
| Talc | From about 10% to about 35%; also from about 17% to about 30%; and also from about 20% to about 25% |
| Titanium Dioxide | From about 15% to about 35%; also from about 20% to about 30%; and also from about 23% to about 28% |
| Zinc Oxide | From about 1% to about 10%; also from about 2% to about 8%; and also from about 3% to about 5% |

The composition of the present invention does require presence of a polysaccharide such as corn starch, in addition to the zirconium oxide. The talc may be substituted with other diluents/carriers, such as lactose, but the overall percentage of talc along with at least one additional diluent is still in the range of 10%-35% w/w.

For example:

| Dry Mix | % by Weight |
| --- | --- |
| Polysaccharide (for example, corn starch) | From about 15% to about 50%; also from about 25% to about 40%; and also from about 30% to about 35% |
| Zirconium Oxide | From about 7% to about 25%; also from about 10% to about 20%; and also from about 13% to about 15% |
| Talc | From about 1% to about 10%; also from about 3% to about 8%; and also from about 5% to about 7% |
| Lactose | From about 9% to about 25%; also from about 14% to about 22%; and also from about 15% to about 18% |
| Titanium Dioxide | From about 15% to about 35%; also from about 20% to about 30%; and also from about 23% to about 28% |
| Zinc Oxide | From about 1% to about 10%; also from about 2% to about 8%; and also from about 3% to about 5% |

Inclusion of a polysaccharide improves the tackiness of the powder composition. In addition, with the use of a polysaccharide, the use of the polysorbate liquid adhesive as a pretreatment to the tooth is now only an optional step, left to the discretion of the technician operating the imaging device, due to some inherent problems with the surface area of the tooth to be imaged. Thus, the use the powder of the present invention can circumvent the initial coating step which now enables the user to image the tooth in simply one step with an application of the powder mixture only. In addition, the powder of the present invention is easier to remove because of the absence of polysorbate liquid adhesive. Finally, cost is reduced because there is no need to purchase a polysorbate liquid.

Another aspect of this invention is the particle size of the imaging powder. In one embodiment, about 90% of the powder has a particle size equal to or less than about 40 microns. In another embodiment, 90% of the powder has a particle size equal to or less than 20 about microns.

The powder may be applied via any air-based method as described above. The PSI required for the air stream will be that as typically recognized in the art. Further, the powder may be applied using a mechanical sprayer device such as that described by U.S. patent application 20050233280, which is herein incorporated by reference.

Method of Mixing

Ingredients are added sequentially and one should sift each through a sifter into a large container. After the addition of each ingredient, the ingredients are mixed together.

Once all ingredients are added sequentially, the final resulting composition is also sifted again. The resulting product is placed in an air-tight container as any moisture or dampness affects the dryness of the powder thus making it clumpy and affecting the flow of the powder.

Method of Application

To apply to the tooth, the imaging powder is placed in an appropriate receptacle and delivered to the surface of the tooth via a stream of compressed air. Currently, methods include a Powder Meister,® Powder Perfect,® Canned Air® or alternatively, by an attachment to a high speed end of a dental unit which allows compressed air to push through the air line and into a bottle containing the imaging powder and subsequently flow out of a nozzle via the compressed air stream to coat the tooth. The flow-through methods of delivery are better when the powder is not too thin or too thick. The air pressure for all methods of delivery is a factor as well and it will be obvious to one skilled in the art as to the required airflow for proper depth of coating of the tooth with the imaging powder in order for suitable imaging to take place and a usable image obtained. If the powder coating on the tooth is thin, then the air pressure (PSI) should be decreased. If powder coating on the tooth is too thick then one must increase the PSI to decrease the thickness of the powder coating on the tooth.

Once a suitable image has been obtained, the powder is removed from the tooth surface by spraying water onto the tooth a suctioning the residue out of the mouth.

What is claimed is:

1. An imaging powder for providing a uniform reflective surface for use in a CAD/CAM device comprising from about 15% to about 50% w/w of a polysaccharide, from about 7% to about 25% w/w of zirconium oxide, from about 1% to about 10% w/w talc, from about 9% to about 25% w/w lactose, from about 15% to about 35% w/w titanium dioxide, and from about 1% to about 10% w/w zinc oxide wherein the powder is capable of adhering to a surface in the oral cavity in the absence of a polysorbate liquid.

2. The imaging powder of claim 1 wherein about 90% of the powder composition has a particle size equal to or less than about 40 microns.

3. The imaging powder of claim 1 wherein about 90% of the powder composition has a particle size equal to or less than about 20 microns.

4. The imaging powder of claim 1, wherein the polysaccharide is from about 25% to about 40% w/w, the zirconium oxide is from about 10% to about 20% w/w, the talc is from about 3% to about 8% w/w, the lactose is from about 14% to about 22% w/w, the titanium dioxide from about 20% to about 30% w/w, and the zinc oxide is from about 2% to about 8% w/w.

5. The imaging powder of claim 1, wherein the polysaccharide is from about 30% to about 35% w/w, the zirconium oxide is from about 13% to about 15% w/w, the talc is from about 5% to about 7% w/w, the lactose is from about 15% to about 18% w/w, the titanium dioxide from about 23% to about 28% w/w, and the zinc oxide is from about 3% to about 5% w/w.

6. The imaging powder of claim 5 wherein the polysaccharide is corn starch.

7. The imaging powder of claim 5 wherein about 90% of the powder composition has a particle size equal to or less than about 40 microns.

8. The imaging powder of claim 5 wherein about 90% of the powder composition has a particle size equal to or less than about 20 microns.

9. The imaging powder of claim 6 wherein about 90% of the powder composition has a particle size equal to or less than about 20 microns.

10. The imaging powder of claim 1 which is applied to a tooth via a stream of compressed air, wherein the applied powder is of appropriate thickness in order to obtain a suitable image using a CAD/CAM device.

11. The imaging powder of claim 10, wherein the polysaccharide is corn starch.

12. An imaging powder for use in a CAD/CAM device comprising from about 15% to about 50% w/w of a polysaccharide, from about 7% to about 25% w/w of zirconium oxide, from about 1% to about 10% w/w talc, from about 9% to about 25% w/w lactose, from about 15% to about 35% w/w titanium dioxide, and from about 1% to about 10% w/w zinc oxide, wherein the polysaccharide is corn starch and about 90% of the powder composition has a particle size equal to or less than about 20 microns, wherein the powder is applied to a tooth via a stream of compressed air, and the applied powder is of appropriate thickness in order to obtain a suitable image of the tooth using the CAD/CAM device.

13. An imaging powder for use in a CAD/CAM device comprising from about 30% to about 35% w/w of a polysaccharide, about 13% to about 15% w/w of zirconium oxide, about 20% to about 25% w/w talc, from about 23% to about 28% w/w titanium dioxide, and from about 3% to about 5% w/w zinc oxide, wherein the polysaccharide is corn starch and about 90% of the powder composition has a particle size equal to or less than about 40 microns, wherein the powder is applied to a tooth via a stream of compressed air, and the applied powder is of appropriate thickness in order to obtain a suitable image of the tooth using the CAD/CAM device.

* * * * *